United States Patent [19]

Hall et al.

[11] Patent Number: 4,774,353

[45] Date of Patent: Sep. 27, 1988

[54] TRIORGANOTIN CATALYST PROMOTERS FOR HYDROCYANATION

[75] Inventors: William T. Hall; Ronald J. McKinney; William A. Nugent, all of Wilmington, Del.

[73] Assignee: E. I. Du Pont de Nemours and Company, Wilmington, Del.

[21] Appl. No.: 870,895

[22] Filed: Jun. 5, 1986

[51] Int. Cl.$^4$ .................. C07C 121/20; C07C 121/26
[52] U.S. Cl. ................................. 558/335
[58] Field of Search .............................. 558/335, 338

[56] References Cited

U.S. PATENT DOCUMENTS

| | | | |
|---|---|---|---|
| 2,571,099 | 10/1951 | Arthur et al. | 260/465.3 |
| 3,496,217 | 2/1970 | Drinkard, Jr. et al. | 558/338 |
| 3,496,218 | 2/1970 | Drinkard et al. | 260/465.8 |
| 3,852,325 | 12/1974 | King | 260/465.9 |
| 3,925,445 | 12/1975 | King et al. | 260/465 R |
| 4,082,811 | 4/1978 | Shook, Jr. | 260/606.5 B |
| 4,215,068 | 7/1980 | Wu et al. | 558/338 |

OTHER PUBLICATIONS

Nugent, W. A., et al., "Solvated Triorganotin Cations, Structure and Use as Catalysts for Diels-Alder Additions to Furan", *Organometallics*, 1984, vol. 3, pp. 1315-1317.

Tolman, C. A., et al., "Homogeneous Nickel-Catalyzed Olefin Hydrocyanation," *Advances in Catalysis*, vol. 33, pp. 1-46.

*Primary Examiner*—Anton H. Sutto

[57] ABSTRACT

Zerovalent nickel catalyzed hydrocyanation of mononitriloolefins e.g., 4-pentenenitrile, to dinitriles, e.g., adiponitrile, is improved by using a triorganotin compound as a promoter for the zerovalent nickel.

6 Claims, No Drawings

TRIORGANOTIN CATALYST PROMOTERS FOR HYDROCYANATION

BACKGROUND OF THE INVENTION

1. Field of the Invention

This invention relates to the hydrocyanation of unsaturated nitriles, e.g., 3- and 4-pentenenitriles using a zerovalent nickel catalyst promoted by triorganotin compounds.

2. Description of Related Art

U.S. Pat. No. 2,571,099, issued on Oct. 16, 1951 to Paul Arthur, Jr. et al. discloses the use of nickel carbonyl with or without the addition of a tertiary aryl phosphine or arsine. This process produces a relatively high percentage of undesirable polymeric products when applied to nonconjugated olefinic starting materials and a relatively poor yield in all cases.

U.S. Pat. No. 3,496,217 issued on Feb. 17, 1970 to W. C. Drinkard et al. discloses an improvement in hydrocyanation using a large number of metal cation compounds with a variety of anions as catalyst promoters. More particularly, the patent discloses as a promoter a cation of zinc, cadmium, beryllium, aluminum, gallium, indium, silver, titanium, zirconium, hafnium, germanium, tin, vanadium, niobium, scandium, chromium, molybdenum, tungsten, manganese, rhenium, palladium, thorium, erbium, iron and cobalt, or mixtures thereof. Preferred anions are halide, i.e., fluoride, chloride, bromide, and iodide; anions of lower fatty acids of from 2 to 7 carbon atoms, $HPO_3^{-2}$, $H_2PO_2^{-}$, $CF_3COO^{-}$, $OSO_2C_7F_{15}^{-}$ and $SO_4^{-}$, etc. The known organometallic compounds $(C_2H_5)_3Al_2Cl_3$, and $C_2H_5AlCl_2$ are also disclosed as promoters.

U.S. Pat. No. 3,496,218 issued on Feb. 17, 1970 to W. C. Drinkard discloses a nickel hydrocyanation catalyst promoted with various boron-containing compounds, including triphenylboron and alkali metal borohydrides.

U.S. Pat. No. 3,925,445 issued on Dec. 9, 1975 to C. M. King et al. discloses zerovalent nickel hydrocyanation catalysts promoted with metal halides and organoboron compounds.

U.S. Pat. No. 3,852,325 issued on Dec. 3, 1974 to C. M. King teaches that along with production of 3-pentenenitrile (3PN) in the hydrocyanation of butadiene there is also obtained varying amounts of cis- and trans-2-pentenenitriles (C-2PN and T-2PN) and that these 2-pentenenitriles are found to be detrimental to catalyst efficiency in the hydrocyanation of 3PN or 4-pentenenitrile (4PN) to adiponitrile (ADN). The patentee also teaches that T-2PN cannot be removed satisfactorily from a mixture of pentenenitriles by fractional distillation, for example, because its boiling point is too close to that of other pentenenitriles such as 3PN or 4PN. Isomerizing T-2PN to the more volatile C-2PN which in turn can be removed from the reaction mixture by fractional distillation is discussed.

A recent description of a hydrocyanation process can be found in U.S. Pat. No. 4,082,811 issued on Apr. 4, 1978.

A general discussion of triorganotin compounds and their use a catalysts for the Diels-Alder addition is found in an article by W. A. Nugent et al. appearing in *Organometallics*, Vol. 3, No. 8, pp. 1315–17 (1985). The function of the Lewis acid $\phi_3SnO_2CCF_3$ as a catalyst for the isomerization but not hydrocyanation of 3PN is discussed in the article by C. A. Tolman et al. entitled "Homogenous Nickel Catalyzed Olefin Hydrocyanation", *Advances in Catalysts*, 33, pp. 1–46 (1985).

SUMMARY OF THE INVENTION

The present invention is a process for the preparation of dinitriles, e.g., adiponitrile by the addition of hydrogen cyanide to nonconjugated, unsaturated nitriles e.g., 3- and/or 4-pentenenitriles in the presence of a zerovalent nickel catalyst and a triorganotin catalyst promoter having the general formula

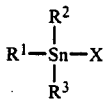

wherein $R^1$, $R^2$ and $R^3$ are the same or different and are selected from groups consisting of alkyl and substituted alkyl groups of 2 to 18 carbon atoms, aryl and substituted aryl groups of 6 to 16 carbon atoms. One or more of the substituent groups in the substituted alkyl and aryl groups are selected from fluoro, alkoxy groups having 1 to 8 carbon atoms, carboalkoxy groups having 1 to 10 carbon atoms, trialkylsilyl groups with alkyls having 1 to 6 carbon atoms, cyanoalkyl groups having 1 to 20 carbon atoms, and sulfonato. The anion X is a non-nucleophilic ion, the conjugate acid of which has a $pK_a$ less than about 4. Specific examples of X include fluoroalkylsulfonates having 1 to 18 carbon atoms; perfluorocarboxylates having 2 to 18 carbons; organo(cyano)metallates of the general formula

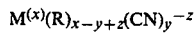

where M is a metal selected from the main metals of Groups IIA, IIIA, IVA and VA of the Periodic Table of the Elements and transition metals of Groups IB, IIB, IIIB, IVB, VB, VIB, VIIB and VIII and where x is the formal oxidation state of the metal and where y is equal to or less than x+z, and where z is usually 1, 2 or 3, and R is an alkyl group of 1 to 8 carbons or an aryl group of 6 to 16 carbons; perhalometallate groups of Group IIIA and VA metals; alkylsulfonate groups having 1 to 12 carbon atoms; arylsulfonate groups having 6 to 18 carbon atoms; substituted alkylsulfonates having 1 to 24 carbon atoms; substituted arylsulfonates having 6 to 28 carbon atoms; fluorosulfonate; sulfate; and perchlorate.

Specifically preferred anions include $BF_4^-$, $SbF_6^-$, $PF_6^-$, $CF_3SO_3^-$, $SO_4^{-2}$, $HSO_4^-$, $ClO_4^-$, $CF_3CO_2^-$, $CH_3C_6H_4SO_3^-$, $CH_3SO_3^-$, $C_{12}H_{25}C_6H_4SO_3^-$, and $B(C_6H_5)_3CN^-$.

DETAILED DESCRIPTION OF THE INVENTION

The present invention can be employed to produce a variety of dinitriles but adiponitrile (ADN) is of particular interest because it is an intermediate used in the production of hexamethylenediamine which in turn is used to produce polyhexamethyleneadipamide, a commercial polyamide useful in forming fibers, films and molded articles.

Although the hydrocyanation reaction can employ any nonconjugated, ethylenically unsaturated organic nitrile of from 4 to 20 carbon atoms, it is of particular interest in the hydrocyanation of pentenenitriles, e.g., 3PN, 4PN and mixtures thereof because these compounds produce ADN.

The catalysts employed for hydrocyanation are zerovalent nickel (Ni°) compounds free of carbon monoxide which may be preformed or prepared in situ and include nickel compounds containing ligands such as alkyl or aryl groups (either of which groups can contain up to 18 carbon atoms) phosphines, arsines, stibines, phosphites, arsenites, stibites, and mixtures thereof.

An especially preferred group of these Ni° compounds have the general structure:

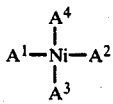

where $A^1$, $A^2$, $A^3$, and $A^4$ are neutral ligands which may be the same or different and have the formula P(XYZ) wherein X and Y are selected from the class consisting of R and OR, and Z has the formula OR, wherein the three R's may be the same or different, and wherein R is selected from the class consisting of alkyl and aryl groups containing up to 18 carbon atoms with aryl being preferred. An especially desirable class of R's are

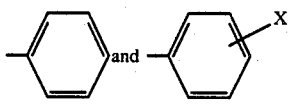

wherein X is selected from the class consisting of Cl, $OCH_3$ and $CH_3$. The R's may be cojoined where possible. The preferred neutral ligands of this group are the aryl phosphites such as triphenyl phosphite, tri-(m- and p-chlorophenyl) phosphite, tri-(m- and p-methoxyphenyl) phosphite and tri-(m- and p-tolyl) phosphite and mixtures thereof. One or more of $A^1$, $A^2$, $A^3$ or $A^4$ may become disassociated from the nickel during the reaction.

The ligands useful in forming the catalyst here may be defined as any atoms or molecules capable of functioning as a sigma and/or pi bonded partner in one or more coordinate bonds. A description of such ligands may be found in *Advanced Inorganic Chemistry* by F. Albert Cotton and G. Wilkinson, published by Interscience Publishers, a division of John Wiley & Sons, Library of Congress Catalog Card No. QD 151.2 C68 (1972) (3rd Edition, 1972, Chapters 21-23).

A particularly preferred group within the foregoing (Ni°) catalysts are those found in U.S. Pat. No. 3,903,120 issued on Sept. 2, 1975 which can be described by the general formula $NiL_4$ where L is a neutral ligand such as a triaryl phosphite of the formula $P(OAr)_3$ wherein Ar is an aryl group of up to 18 carbon atoms. Illustrative of the aryl groups are methoxyphenyl, tolyl, xylyl and phenyl. Meta- and para-tolyl and mixtures thereof are the preferred aryl groups. Excess ligand can be employed.

The promoters to which the present invention is directed are triorganotin compounds and more specifically, those described by the formula

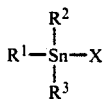

wherein $R^1$, $R^2$ and $R^3$ are the same or different and are selected from groups consisting of alkyl and substituted alkyl groups of 2 to 12 carbon atoms, aryl and substituted aryl groups of 6 to 16 carbon atoms. One or more of the substituent groups in the substituted alkyl and aryl groups are selected from fluoro, alkoxy groups having 1 to 8 carbon atoms, carboalkoxy groups having 1 to 10 carbon atoms, trialkylsilyl groups with alkyls having 1 to 6 carbon atoms, cyanoalkyl groups having 1 to 20 carbon atoms, and sulfonato. The anion, X, comprises a non-nucleophilic ion whose conjugate acid has a $pK_a$ less than about 4. Anions (X) included in the above formula are groups selected from the class consisting of fluoroalkylsulfonates having 1 to 18 carbon atoms; perfluorocarboxylates having 2 to 18 carbons; organo(cyano)metallates of the general formula

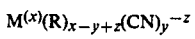

where M is a metal selected from the main metals of Groups IIA, IIIA, IVA and VA of the Periodic Table of the Elements and transition of Groups IB, IIB, IIIB, IVB, VB, VIB, VIIB and VIII and where x is the formal oxidation state of the metal and where y is equal to or less than x+z, and where z is usually 1, 2 or 3, and R is an alkyl group of 1 to 8 carbons or an aryl group of 6 to 16 carbons; perhalometallate groups of Group III and V metals; alkylsulfonate groups having 1 to 12 carbon atoms; arylsulfonate groups having 6 to 18 carbon atoms; substituted alkylsulfonates having 1 to 24 carbon atoms; substituted arylsulfonates having 6 to 28 carbon atoms; fluorosulfonate; sulfate; perchlorate. More particularly the foregoing includes $BF_4^-$, $SbF_6^-$, $PF_6^-$, $CF_3SO_3^-$, $SO_4^=$, $HSO_4^-$, $ClO_4^-$, $CF_3CO_2^-$, $CH_3C_6H_4SO_3^-$, $CH_3SO_3^-$, $C_{12}H_{25}C_6H_4SO_3^-$, $B(C_6H_5)_3CN^-$, $C_{12}F_{25}C_6F_4CO_2^-$ and $B(C_6H_5)_4^-$, preferably $CF_3SO_3^-$, $SO_4^=$, $HSO_4^-$, $CH_3C_6H_4SO_3^-$, $CH_3SO_3^-$, $C_{12}H_{25}C_6H_4SO_3^-$, $ClO_4^-$, $CF_3CO_2$, $B(C_6H_5)_3CN^-$, $C_{12}F_{25}C_6F_4CO_2^-$, and $B(C_6H_5)_4^-$. The groups most preferred are $SO_4^=$, $HSO_4^-$, $CH_3SO_3^-$, $CH_3C_6H_4SO_3^-$, $C_{12}H_{25}C_6H_4SO_3^-$, and $B(C_6H_5)_3CN^-$. Specific examples of the foregoing include $(C_2H_5)_3Sn(SbF_6)$, $(C_6H_5)Sn(CF_3CO_2)$, $C(_{12}H_{25})_3Sn(CF_3SO_3)$, $(C_{10}H_{21}C_6H_4)Sn(O_3SCF_3)$, $(C_3H_7)_3Sn(BF_4)$, $(CH_3OC_6H_4)_3Sn(CF_3CO_2)$, (neo-$C_5H_{11})_3Sn(CF_3CO_2)$, $(C_8H_{17}OC_6H_4)_3Sn(CF_3CO_2)$, (cy-$C_6H_{11})_3Sn(ClO_4)$, $(FC_6H_4)_3Sn(SbF_6)$, $(C_6H_5CH_2)_3Sn(SbF_6)$, $(CH_3C_6H_4)_3Sn(CF_3CO_2)$, $\{(CH_3)_3SiCH_2\}_3Sn(SbF_6)$, $(NaSO_3C_6H_4)_3Sn$-$(O_3SC_6H_4CH_3)$, $\{(C_6H_{13})_3SiCH_2\}_3Sn(PF_6)$, $(C_6H_5)_3Sn(O_2CC_6F_4C_{12}F_{25})$, $(C_6H_5)_3Sn(AlCl_4)$, $(C_6H_5)_3Sn(O_4SH)$, $\{(cy-C_6H_{11})_3Sn\}_2\{Zn(CN)_4\}$, $\{(C_6H_5)_3Sn\}_2(SO_4)$, $\{(C_4H_9)_3Sn\}_3\{Co(CN)_6\}$, $\{(C_6H_5)_3Sn\}_3\{Fe(CN)_6\}$, $\{(C_4H_9)_3Sn\}_2\{Ni(CN)_4\}$, $(C_6H_5)_3Sn\{B(C_6H_5)_3CN\}$ and $(C_2H_5)_3Sn\{B(C_6H_5)_4\}$.

The above described triorganotin promoters are easily handled in air due to their low sensitivity to atmospheric oxygen and consequently do not require costly handling procedures. Typical preparative procedures for the triorganotin compounds are described in the following references: Burg and Spielman, *J. Am. Chem. Soc.*, 83, pp. 2667–2668 (1961); Treichel and Goedrich, *Inorg. Chem.*, 4, pp. 1424–1427 (1965); Okawara, Hathaway and Webster, *Proc. Chem. Soc.*, pp. 13–14 (1963); Clark and O'Brien, *Inorg. Chem.*, 2, pp. 740–744 (1963); Clark and Goel, *Inorg. Chem.*, 4, pp. 1428–1432 (1965); W. A. Nugent, et al., *Organometallics*, 3, 1315 (1985);

and R Uson, et al., *J. Organomet. Chem.*, 185, 359 (1980).

The hydrocyanation reaction can be carried out by charging a reactor with all of the reactants or preferably the reactor is charged with the catalyst, or catalyst components, the unsaturated organic compound, the promoter and whatever solvent is to be used and the hydrogen cyanide gas is swept over the surface of the reaction mixture or bubbled through said reaction mixture. Another technique is to charge the reactor with the catalyst, promoter, hydrogen cyanide and whatever solvent is to be used and feeding the unsaturated compound slowly to the reaction mixture.

Preferably, the hydrocyanation is conducted continuously in one or more agitated steps or stages. If a plurality of stages is employed, it is preferred that the stages be in series with the product from one stage being directed to a subsequent stage. The hydrogen cyanide can be introduced into the first stage or split between stages.

The hyrocyanation reaction can be carried out with or without a solvent. The solvent should be liquid at the reaction temperature and pressure and inert towards the unsaturated compound and the catalyst. Generally, such solvents are hydrocarbons such as benzene or xylene, or nitriles such as acetonitrile or benzonitrile but, preferably, the ligand serves as the solvent.

Although the following discussion is directed to the hydrocyanation of 3PN and/or 4PN to produce ADN using Ni° catalyst containing a mixed tri-m,p-tolyl phosphite ligand with a triorganotin compound as a promoter, it is understood that it applies to other types of nitriles and Ni° catalysts.

The following examples are presented to illustrate but not to restrict the present invention. The nitrile fed was 3PN which had been fractionally distilled to remove water and substantially reduce C-2PN. In the Table, distribution is reported as moles of ADN produced, divided by the total moles of dinitrile products, multiplied by 100. The 2PN yield is reported as the total moles of 2PN produced divided by the total moles of 3PN reacted, multiplied by 100. The ADN yield is reported as the total moles of ADN produced, divided by the sum of the total moles of dinitrile products and the total moles of 2PN multiplied by 100.

EXAMPLES 1-34

A catalyst solution was prepared by combining Ni[P-(O-p-tolyl)$_3$]$_4$ (2.94 g, 2.0 mmol), P(O-p-tolyl)$_3$ (2.50 cc; 8.3 mmol), and benzonitrile (2.50 cc; internal standard) were dissolved in 3-pentenenitrile (95 cc; 1.0 mmol). One molar equivalent of the triorganotin promoter indicated in the Table per mole of Ni° was added to a 10 cc aliquot of the catalyst solution in a glass, 3-neck round bottom flask fitted with a magnetic stirring bar, rubber septum, reflux condenser and nitrogen bubbler and the mixture heated to 50°–55° C. in a thermostatically controlled oil bath. Hydrogen cyanide was then fed to the mixture by vapor transfer, i.e., nitrogen gas was passed through liquid hydrogen cyanide cooled to 0° C. to produce a saturated vapor mixture having approximately 30–40% hydrogen cyanide. The hydrogen cyanide vapor was admitted to the reaction vessel just above the liquid level and the vapor absorbed into the reaction mixture.

Analyses of reaction mixtures with time were carried out by removing samples with a syringe, diluting with acetone and analyzing by capillary gas chromatography (Carbowax ® 20M capillary column, 25 m, 0.2 mm inner diameter). Concentrations of reagents and products were determined by comparing with the internal standard, benzonitrile, for which response factors had been previously calculated.

TABLE

| Example | Organotin Promoter (R$_3$SnX) R | X | Distribution | Yield 2-PN | ADN |
|---|---|---|---|---|---|
| 1 | C$_2$H$_5$ | SbF$_6$ | 83 | 1.5 | 81.5 |
| 2 | n-C$_3$H$_7$ | SbF$_6$ | 84 | 2 | 82 |
| 3 | n-C$_3$H$_7$ | SbF$_6$ | 82 | 2.5 | 79.5 |
| 4 | i-C$_3$H$_7$ | SbF$_6$ | 88.5 | 2 | 86.5 |
| 5 | | BF$_4$ | 84 | 2 | 82 |
| 6 | | CF$_3$SO$_3$ | 84 | 2.5 | 81.5 |
| 7 | | CF$_3$CO$_2$ | 85.5 | 2 | 83.5 |
| 8 | i-C$_4$H$_9$ | SbF$_6$ | 82 | 2.5 | 79.5 |
| 9 | sec-C$_4$H$_9$ | SbF$_6$ | 88 | 1.5 | 86.5 |
| 10 | t-C$_4$H$_9$ | SbF$_6$ | 87 | 1 | 86 |
| 11 | neo-C$_5$H$_{11}$ | SbF$_6$ | 88 | 2 | 86 |
| 12 | | CF$_3$SO$_3$ | 88 | 3 | 85 |
| 13 | | CF$_3$CO$_2$ | 90 | 2 | 88 |
| 14 | cy-C$_6$H$_{11}$ | SbF$_6$ | 90 | 3 | 87 |
| 15 | | CF$_3$SO$_3$ | 90 | 3 | 87 |
| 16 | | ClO$_4$ | 91 | 2 | 89 |
| 17 | | CF$_3$CO$_2$ | 91.5 | 2.5 | 89 |
| 18 | C$_6$H$_5$CH$_2$ | SbF$_6$ | 81 | 2 | 79 |
| 19 | | CF$_3$CO$_2$ | 83 | 2 | 81 |
| 20 | (CH$_3$)$_3$SiCH$_2$ | SbF$_6$ | 83 | 2 | 81 |
| 21 | C$_6$H$_5$(CH$_3$)$_2$CCH$_2$ | CF$_3$CO$_2$ | 88 | 4 | 84 |
| 22 | C$_6$H$_5$ | PF$_6$ | 88 | 3 | 85 |
| 23 | | SbF$_6$ | 84 | 1 | 83 |
| 24 | | BF$_4$ | 85 | 2 | 83 |
| 25 | | CF$_3$SO$_3$ | 87 | 1 | 86 |
| 26 | | SO$_4$ | 90 | 2.5 | 87.5 |
| 27 | | CF$_3$CO$_2$ | 91 | 3 | 88 |
| 28 | | CH$_3$C$_6$H$_4$SO$_3$ | 92 | 3 | 89 |
| 29 | | (CH$_3$)$_3$C$_6$H$_2$CO$_2$ | 87 | 5 | 82 |
| 30 | | B(C$_6$H$_5$)$_3$CN | 93 | 2 | 91 |
| 31 | p-CH$_3$OC$_6$H$_4$ | CF$_3$CO$_2$ | 86 | 2 | 84 |
| 32 | p-FC$_6$H$_4$ | SbF$_6$ | 83 | 1 | 82 |
| 33 | | CF$_3$CO$_2$ | 90.5 | 1.5 | 89 |
| 34 | o-CH$_3$C$_6$H$_4$ | CF$_3$CO$_2$ | 84 | 1.5 | 82.5 |

The foregoing illustrates the high ADN yields and low 2PN yields obtainable using triorganotin compounds as promoters in the Ni°-catalyzed hydrocyanation of mononitriles.

We claim:

1. A process for the preparation of dinitriles by the addition of hydrogen cyanide to nonconjugated, unsaturated nitriles having 4 to 20 carbon atoms in the presence of a zerovalent nickel catalyst and a triorganotin catalyst promoter having the general formula

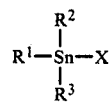

wherein R$^1$, R$^2$ and R$^3$ are the same or different and are selected from groups consisting of alkyl and substituted alkyl groups of 2 to 18 carbon atoms, aryl and substituted aryl groups of 6 to 16 carbon atoms, wherein one or more of the substituent groups are selected from fluoro, alkoxy groups having 1 to 8 carbon atoms, carboalkoxy groups having 1 to 10 carbon atoms, trialkylsilyl groups with alkyls having 1 to 6 carbon atoms, cyanoalkyl groups having 1 to 20 carbon atoms, sulfonato, and nitro, and X is a non-nucleophilic anion, whose conjugate acid has a pK$_a$ less than about 4.

2. The process of claim 1 wherein X is selected from groups consisting of fluoroalkylsulfonates having 1 to 18 carbon atoms; perfluorocarboxylates having 2 to 18 carbons; organo(cyano)metallates of the general formula $$M^{(x)}(R)_{x-y+z}(CN)_y{}^{-z}$$

where M is a main group or transition metal and where x is the formal oxidation state of the metal, y is equal to or less than x+z, and where z is usually 1, 2 or 3, and R is a group selected from the class consisting of an alkyl group of 1 to 8 carbon atoms and aryl groups of 6 to 16 carbons; perhalometallates of Group IIIA and VA metals; alkylsulfonates having 1 to 12 carbon atoms; arylsulfonates having 6 to 18 carbon atoms; substituted alkylsulfonates having 1 to 24 carbon atoms; substituted arylsulfonates having 6 to 28 carbon atoms; fluorosulfonate; sulfate; and perchlorate.

3. The process of claim 2 wherein X is a group selected from the class consisting of $BF_4{}^-$, $SbF_6{}^-$, $PF_6{}^-$, $CF_3SO_3{}^-$, $SO_4{}^=$, $HSO_4{}^-$, $ClO_4{}^-$, $CF_3CO_2{}^-$, $CH_3C_6H_4SO_3{}^-$, $CH_3SO_3{}^-$, $C_{12}H_{25}C_6H_4SO_3{}^-$, $B(C_6H_5)_3CN^-$, $C_{12}F_{25}C_6F_4CO_2{}^-$ and $B(C_6H_5)_4{}^-$.

4. The process of claim 2 wherein X is a group selected from the class consisting of $CF_3SO_3{}^-$, $SO_4{}^=$, $HSO_4{}^-$, $CH_3C_6H_4SO_3{}^-$, $CH_3SO_3{}^-$, $C_{12}H_{25}C_6H_4SO_3{}^-$, $ClO_4{}^-$, $CF_3CO_2{}^-$, $B(C_6H_5)_3CN^-$, $C_{12}F_{25}C_6F_4CO_2{}^-$ and $B(C_6H_5)_4{}^-$.

5. The process of claim 2 wherein X is a group selected from the class consisting of $SO_4{}^-$, $HSO_4$, $CH_3SO_3{}^-$, $CH_3C_6H_4SO_3{}^-$, $C_{12}H_{25}C_6H_4SO_3{}^-$, and $B(C_6H_5)_3CN^-$.

6. The process of claim 1 wherein the promoter is $(C_6H_5)_3Sn\{B(C_6H_5)_3CN\}$.

* * * * *